US010485960B2

(12) United States Patent
Patadia

(10) Patent No.: US 10,485,960 B2
(45) Date of Patent: Nov. 26, 2019

(54) SYSTEM AND METHOD FOR DEPLOYING A PROXIMALLY-FLARING STENT

(76) Inventor: Bipin C. Patadia, Upland, CA (US)

(*) Notice: Subject to any disclaimer, the term of this patent is extended or adjusted under 35 U.S.C. 154(b) by 1687 days.

(21) Appl. No.: 11/993,951

(22) PCT Filed: Jun. 29, 2005

(86) PCT No.: PCT/US2005/023267
§ 371 (c)(1),
(2), (4) Date: Jun. 4, 2010

(87) PCT Pub. No.: WO2007/005010
PCT Pub. Date: Jan. 11, 2007

(65) Prior Publication Data
US 2010/0241210 A1  Sep. 23, 2010

(51) Int. Cl.
*A61F 2/06* (2013.01)
*A61M 25/10* (2013.01)

(52) U.S. Cl.
CPC .... *A61M 25/1027* (2013.01); *Y10T 29/49826* (2015.01)

(58) Field of Classification Search
CPC ....... A61M 25/1027; A61F 2/86; A61F 2/958; A61F 2230/0054; A61F 2250/0067; A61F 2250/0048; A61F 2002/821; Y10T 29/49826
USPC ...................................... 623/1.11–1.23, 1.35
See application file for complete search history.

(56) References Cited

U.S. PATENT DOCUMENTS

| 4,994,066 | A | * | 2/1991 | Voss ............................. 606/108 |
| 5,607,444 | A | * | 3/1997 | Lam ............................. 606/194 |
| 5,624,411 | A | * | 4/1997 | Tuch ............................ 604/265 |
| 5,632,762 | A |   | 5/1997 | Myler et al. |
| 5,645,560 | A |   | 7/1997 | Crocker et al. |
| 5,868,777 | A | * | 2/1999 | Lam ............................. 606/194 |
| 6,096,071 | A | * | 8/2000 | Yadav ......................... 623/1.15 |
| 6,346,089 | B1 | * | 2/2002 | Dibie .......................... 623/1.15 |
| 6,481,262 | B2 | * | 11/2002 | Ching et al. ................... 72/416 |
| 7,105,015 | B2 | * | 9/2006 | Goshgarian ................. 623/1.11 |
| 7,481,834 | B2 | * | 1/2009 | Kaplan et al. .............. 623/1.15 |
| 7,582,111 | B2 | * | 9/2009 | Krolik et al. ............... 623/1.32 |
| 7,758,630 | B2 | * | 7/2010 | Davis et al. ................ 623/1.16 |
| 8,015,684 | B2 | * | 9/2011 | Pacetti ........................ 29/283.5 |
| 8,020,273 | B2 | * | 9/2011 | Pacetti ........................... 29/447 |
| 8,109,987 | B2 | * | 2/2012 | Kaplan et al. .............. 623/1.15 |

(Continued)

FOREIGN PATENT DOCUMENTS

WO    93/15775    8/1993
WO    93/16479    8/1993

(Continued)

*Primary Examiner* — Amy R Weisberg
(74) *Attorney, Agent, or Firm* — K&L Gates LLP; Louis C. Cullman; Georgia N. Kefallinos

(57) ABSTRACT

Disclosed herein are proximally-flaring stents and balloon catheter systems and methods for using the same to restore patency to a side branch and its ostium at a vessel bifurcation, where the side branch can only be approached from the direction of the main artery. The system and methods include a proximally-flaring stent (10) and one or more balloon catheters (250, 400) with inflatable balloons that are able to push a flanged proximal portion (40) of the proximally-flaring stent entirely against the artery walls of the main artery of the side branch so that blood flow is not occluded.

20 Claims, 3 Drawing Sheets

(56) References Cited

U.S. PATENT DOCUMENTS

| | | | |
|---|---|---|---|
| 8,257,432 B2 * | 9/2012 | Kaplan et al. | 623/1.35 |
| 2002/0087153 A1 | 7/2002 | Roschak et al. | |
| 2002/0116047 A1 * | 8/2002 | Vardi et al. | 623/1.11 |
| 2004/0254627 A1 * | 12/2004 | Thompson et al. | 623/1.11 |
| 2007/0179592 A1 * | 8/2007 | Schaeffer | 623/1.35 |
| 2008/0243233 A1 * | 10/2008 | Ben-Muvhar et al. | 623/1.35 |
| 2009/0259299 A1 * | 10/2009 | Moloney | 623/1.35 |
| 2011/0288622 A1 * | 11/2011 | Chan et al. | 623/1.11 |

FOREIGN PATENT DOCUMENTS

| | | |
|---|---|---|
| WO | 2005034807 | 4/2005 |
| WO | 2005/041810 A2 | 5/2005 |

* cited by examiner

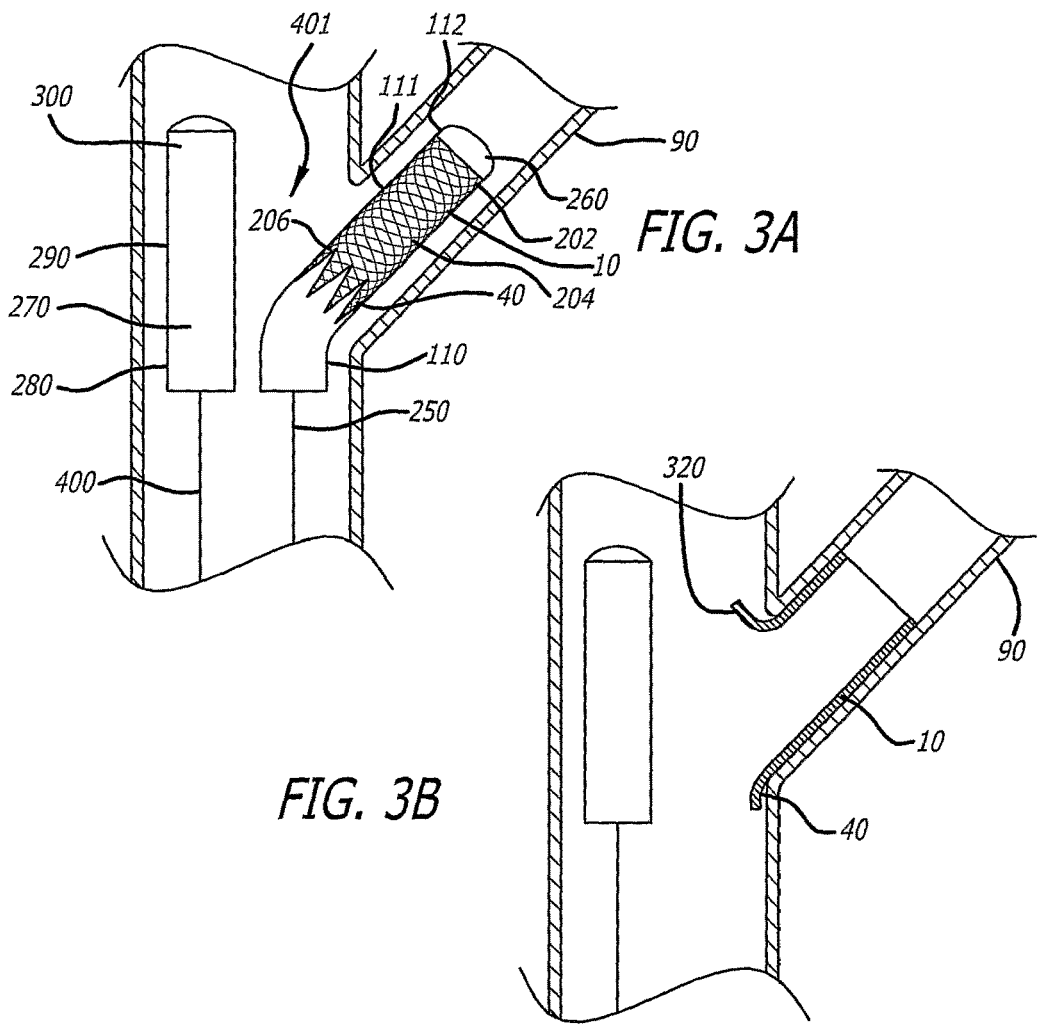
FIG. 3A
FIG. 3B
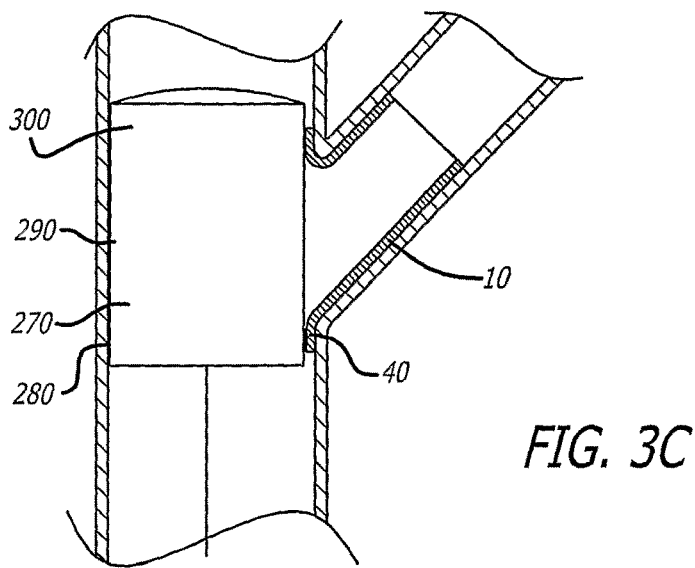
FIG. 3C

SYSTEM AND METHOD FOR DEPLOYING A PROXIMALLY-FLARING STENT

CROSS REFERENCE TO RELATED APPLICATIONS

The present application is an application under section 371 of International Patent Application PCT/US2005/023267 filed on Jun. 29, 2005, the entire contents of which is hereby incorporated by reference.

FIELD OF THE INVENTION

The present invention relates to proximally-flaring stent and balloon catheter systems and methods for using the systems to restore patency to a side branch and its ostium at a vessel bifurcation where the side branch only can be approached in the direction of blood flow rather than in the direction opposite of blood flow (i.e. from the direction of the main artery). This invention also can be used for any ostium or any opening where an ostium must be approached from its main conduit (i.e., the duodenum and bile duct). Thus, the present invention can be used to approach any ostium or opening from its main conduit.

BACKGROUND OF THE INVENTION

Stents are ridged, or semi-ridged, tubular scaffoldings that are deployed within the lumen (inner tubular space) of a vessel or duct during angioplasty or related procedures intended to restore patency (openness) to vessel or duct lumens. Stents generally are left within the lumen of a vessel or duct after angioplasty or a related procedure to reduce the risk of restenosis (re-closure).

During angioplasty, an expandable stent typically is mounted over a balloon catheter and positioned at a desired location within the lumen of a vessel or duct. The balloon is inflated temporarily thereby expanding and implanting the stent within the lumen. The balloon then is deflated and removed from the lumen, while the stent is left in place. Because stent and balloon implantation is a relatively non-invasive procedure, it has proven to be a preferable alternative to open heart surgery.

Due to their generally straight and tubular shape, conventional stents can be effective at restoring patency to the lumens of vessels or ducts when the area to be treated is a uniform and relatively straight area of the vessel or duct. Vessels and ducts, however, branch numerous times as they travel throughout the body. When a vessel branches, the opening to the branched vessel is called an ostium. Conventional stents are not adequate to restore patency around ostiums for several reasons. First, in many circumstances, patency must be restored in a main vessel both before and after an ostium at a vessel bifurcation. A conventional stent cannot restore patency both before and after an ostium without covering the ostium itself, thereby "gating" it. Such "gating" generally is not acceptable because it impedes blood flow to the vessel branch. If the ostium is not gated in this manner, however, then patency has not been restored both before and after the ostium with the use of a conventional stent. While two conventional stents can be used to restore patency around an ostium (one before and one after the ostium), this approach leaves the ostium area itself untreated. Second, if the area to be treated extends into the branched portion of the vessel, the conventional stent does not restore patency to the branch because it remains entirely within the main artery. Thus, treatment is incomplete.

One type of stent that has been developed to address the problem of restoring patency near vessel bifurcations is the distally-flaring stent. Distally-flaring stents, as described in U.S. Pat. No. 5,868,777 (the "Lam patent" issued Feb. 9, 1999 and assigned to Advanced Cardiovascular Systems, Santa Clara, Calif.), have one end that is highly malleable and able to conform to the irregular shape of an ostium. When placed on a balloon catheter, and during deployment, the highly-malleable ("flaring" or "flanged" portion) of the stent is positioned on the distal (far) end of the balloon catheter. The distally-flaring stent is advanced in a retrograde fashion (i.e., against the direction of blood flow or towards the branch's main artery) until its distal end is in the immediate vicinity of the ostium of a side branch. The main body of the distally-flaring stent then is expanded within the side branch, while the distally-flaring portion is expanded over the ostium of the branch and, to a small degree, within the main artery. In this manner, the distally-flaring stent may be adequate to restore patency when a lesion is located primarily within a side branch and at an ostium (see FIG. 1) and when the treatment site can be approached from an entry point that is distal to the ostial narrowing (for example the superior or inferior extremity arteries).

While the above described method of using distally-flaring stents can be effective at restoring patency at particular branches, there are many circumstances when the treatment site cannot be approached from a point distal to the ostial narrowing (for example, in the coronary arteries). In these circumstances, the distally-flaring stent is inadequate because if it is advanced in a non-retrograde fashion (i.e., into the side branch from the main artery), and it is positioned within a side branch to restore patency, the distal flaring portion of the stent will have moved beyond the ostium and is no longer in position to expand in the area that it was designed to treat. Instead, once positioned within a side branch, the distally-flaring portion of the stent is confined within the more uniform lumen of the vessel, removed a distance from the irregular shape of the ostium. Thus, in an area of restricted access, such as the coronary arteries (and, as will be explained infra, other lumens as well), a distally-flaring stent is not effective in treating a lesion found within a side branch and ostium. Therefore, a need exists for a stent that is able to expand predominantly within a side branch while still flaring to cover the irregular shape of an ostium when the ostium only can be approached from the direction of the main artery.

Importantly, one may believe that the drawbacks associated with the distally-flaring stent of the Lam patent may be overcome simply by turning the distally-flaring stent around prior to loading it onto a balloon of a balloon catheter. This, however is not the case. Simply turning the distally-flaring stent around does not address the drawbacks associated with distally-flaring stents because this 'solution' does not provide a way to ensure that the flaring portion of the stent will be fully deployed against the interior walls of a main artery. Indeed, when loaded onto a balloon, the distally-flaring stents described in the Lam patent cover substantially the balloon's entire length. This extensive coverage of the balloon by the distally-flaring stent prevents the balloon from inflating meaningfully beyond the stent's proximal end which can prevent the balloon from pushing the proximal end of the stent entirely flush against the ostium thus occluding blood flow in the main artery. The Lam patent does not provide an adequate solution to this problem.

One approach to address the failure to inflate meaningfully beyond the stent's proximal end is to pull the balloon catheter back relative to the position of the stent and inflate the balloon again. Such repositioning of the balloon catheter, however, generally will negatively affect the positioning of the stent. Thus, this approach also does not provide an adequate solution to the above-identified problems.

Based on the preceding discussion, the distally-flaring stents described in the Lam patent can only be used effectively in a manner that is retrograde to the direction of blood flow (for example at ostiums of superior and inferior extremity arteries). The distally-flaring stents described in the Lam patent may be effective in these areas because they may have an entry point that is distal to the ostium. The distally-flaring stents described in the Lam patent cannot, however, be used to treat side branches and ostiums in the coronary arteries or other branches that may only be approached in the direction of blood flow.

SUMMARY OF THE INVENTION

The present invention addresses the above-described problems associated with distally-flaring stents and other prior art methods by providing proximally-flaring stent and balloon catheter systems, as well as methods of their use, that can restore patency at a lesion found at an ostium and within a side branch that can only be approached in the direction of blood flow or from the ostium's main artery or conduit. In use, the proximally-flaring stent is positioned within the side branch of a branched vessel. Unlike the distally-flaring stent described in the Lam patent, the flaring portion of the proximally-flaring stent of the present invention is its proximal end, and therefore it does not pass the ostium when positioned within a side branch. The systems and methods of the present invention also provide effective approaches to ensure that the proximally-flaring portion of the proximally-flaring stent is fully deployed within the main artery so that blood flow is not occluded.

Once positioned within a side branch, several different methods can be used to deploy the proximally-flaring stent of the present invention. In the first deployment method, two balloons are used to fully deploy the proximally-flaring stent. In this deployment method, the majority of the proximally-flaring stent is deployed by a first balloon positioned within a side branch. This balloon in the side branch then is removed, and a second balloon, already positioned within the main artery, is inflated within the main artery to complete deployment of the stent and to ensure that the entirety of the flanged proximal portion of the proximally-flaring stent is pressed flush against the inner walls of the main artery. In this embodiment of the systems and methods of the present invention, the second balloon within the main artery inflates sequentially from its proximal to distal end. In an alternative embodiment adopting this system and deployment method, inflation of the second balloon also can be used to deploy a second stent within the main artery.

In a second system and method of the present invention, one balloon can be used to deploy the proximally-flaring stent of the present invention. In this system and deployment method, the proximally-flaring stent again is mounted over a balloon and positioned within a side branch. In this embodiment, the flanged proximal portion of the proximally-flaring stent is not aligned with the proximal end of the balloon. Instead, the balloon extends proximally beyond the proximally-flaring stent's flanged proximal portion. Because the proximally-flaring stent of the present invention does not overlay the entire balloon of the balloon catheter, but instead leaves a large area uncovered, the balloon is able to push the flanged proximal portion entirely against the artery walls and blood flow is not occluded within the main artery. This deployment method can be achieved with the use of a single compliant balloon which will take the shape of the side branch, ostium, and main artery and push the flanged proximal portion of the proximally-flaring stent against the inner wall of the main artery. While not necessary, in one embodiment, this system and deployment method can use a balloon that sequentially inflates from its distal to proximal end.

By use of the methods just described, patency is restored within a side branch and an ostium. If no treatment is required in the main artery, then the proximally-flaring stent of the present invention, does not leave excess or unnecessary stent material within the lumen of the main artery. If patency must be restored within the main artery, one or more conventional stents can be used before and/or after the ostium.

In one embodiment of the systems of the present invention, the system comprises a proximally-flaring stent and two balloon catheters. In this embodiment, the proximally-flaring stent has a distal portion, a medial region, a hinge area, and a flanged proximal portion. The first balloon catheter includes a first balloon that comprises a distal portion, a medial region, and a proximal portion. The second balloon catheter comprises a second balloon that also comprises a distal portion, a medial region, and a proximal portion. In this embodiment of the system of the present invention the proximally-flaring stent is deployed over the first balloon so that the proximally-flaring stent's proximal portion is proximal to the proximally-flaring stent's distal portion and the proximally-flaring stent's flanged proximal portion is approximately within the medial region of the first inflatable balloon. The second balloon can be sequentially inflated from its proximal portion through its medial region and finally to its distal portion. In this embodiment of the present invention, the first inflatable balloon is not sequentially inflatable. In another embodiment of the present invention, the first inflatable balloon can be sequentially inflatable from its distal portion, through its medial region and finally to its proximal portion. In another embodiment of the system of the present invention, the second balloon also has a stent mounted onto it for deployment within a main artery.

In one embodiment of the systems of the present invention, the system comprises a proximally-flaring stent, and a balloon catheter. The proximally-flaring stent includes a distal portion, a medial region, a hinge area and a flanged proximal portion. The balloon catheter includes an inflatable balloon with a distal portion, a medial region and a proximal portion. In this embodiment of the system of the present invention, the proximally-flaring stent is deployed over the inflatable balloon such that the proximally-flaring stent's flanged proximal portion is proximal to the proximally-flaring stent's distal portion and the proximally-flaring stent's flanged proximal portion is approximately within the medial region of the balloon. In this embodiment of the present invention, the inflatable balloon is not capable of sequential inflation. In another embodiment of the present invention, the balloon is capable of sequential inflation from its distal portion, to its medial region and finally to its proximal portion. In another embodiment of the present invention, the proximal portion of the balloon is more compliant than its distal portion.

In one embodiment of the present invention, the systems are deployed within a side branch of a branched vessel, so that the distal portion and medial region of the proximally-flaring stent expand within the side branch, the hinge area expands at the ostium and the flanged proximal portion of the proximally-flaring stent expands within the main artery giving rise to said side branch.

In one embodiment of the systems of the present invention, the flanged proximal portion of the proximally-flaring stent is approximately 0.25 cm. In another embodiment of the systems of the present invention, the flanged proximal portion of the proximally-flaring stent is approximately 0.5 cm. In another embodiment of the systems of the present invention, the flanged proximal portion of the proximally-flaring stent is approximately 0.75 cm. In another embodiment of the systems of the present invention, the flanged proximal portion of the proximally-flaring stent is approximately 1.0 cm. In another embodiment, the flanged proximal portion of the proximally-flaring stent is between approximately 0.25 cm and approximately 1.0 cm.

In one embodiment of the systems of the present invention, the proximally-flaring stent is made from an elastic metal or polymer. In another embodiment of the systems of the present invention, the proximally-flaring stent is made from a material selected from the group consisting of stainless steel, titanium, nickel-titanium, cobalt-chromium, cobalt-chromium-vanadium, cobalt-chromium-tungsten, gold, silver, platinum and platinum iridium or any combination thereof. In another embodiment of the systems of the present invention, the proximally-flaring stent is made from a material selected from the group consisting of biosorbable polymers, biodegradable polymers, bioerodable polymers and biologically stable polymers.

In one embodiment of the systems of the present invention, the proximally-flaring stent further comprises a bioactive agent. In another embodiment of the systems of the present invention, the proximally-flaring stent further comprises a controlled release coating. In another embodiment of the systems of the present invention, the bioactive agent is selected from the group consisting of antiproliferatives, anti-thrombogenics, anti-coagulates, lubricity enhancing agents, anti-inflammatories, antibiotics, antioxidants and analgesics.

In one embodiment of the systems of the present invention, the balloons are segmented into one or more independently inflatable compartments. In another embodiment of the systems of the present invention, the distal portion of a balloon comprises a first compartment, the medial region of a balloon comprises a second compartment and the proximal portion of a balloon comprises a third compartment. In another embodiment of the systems of the present invention, during treatment of a treatment site with a vessel bifurcation, the compartment of each balloon that is closest to the vessel bifurcation is more compliant than the compartments that are farther from the vessel bifurcation. In another embodiment of the present invention, sequentially-inflatable balloons are made so by exerting different pressures onto different portions of the balloon during crimping onto the balloon catheter.

The present invention also includes methods for making the systems of the present invention. One embodiment of the methods of the present invention include providing a proximally-flaring stent and two balloon catheters. The proximally-flaring stent includes a distal portion, a medial region, a hinge area and a flanged proximal portion. The first balloon catheter includes a first balloon that comprises a distal portion, a medial region, and a proximal portion. The second balloon catheter also comprises a balloon that comprises a distal portion, a medial region, and a proximal portion. In this embodiment of the methods of the present invention, the proximally-flaring stent is deployed over the first balloon such that the proximally-flaring stent's flanged proximal portion is proximal to its distal portion and approximately within the first balloon's medial region. The second balloon can inflate sequentially from its proximal portion through its medial region and finally to its distal portion. In another embodiment of the methods of the present invention, a second stent is included for deployment on the second balloon.

One embodiment of the methods of the present invention includes providing a proximally-flaring stent that includes a distal portion, a medial region, a hinge area and a flanged proximal portion and providing a balloon catheter having an inflatable balloon located at the balloon catheter's distal end. The inflatable balloon has a distal portion, a medial region and a proximal portion. The proximally-flaring stent then is mounted onto the inflatable balloon such that the flanged proximal portion of the proximally-flaring stent does not extend proximally beyond the inflatable balloon's medial portion and the distal portion of the proximally-flaring stent is distal to the flanged proximal portion.

In one embodiment of the methods of the present invention, the flanged proximal portion of the proximally-flaring stent is approximately 0.25 cm. In another embodiment of the methods of the present invention, the flanged proximal portion of the proximally-flaring stent is approximately 0.5 cm. In another embodiment of the methods of the present invention, the flanged proximal portion of the proximally-flaring stent is approximately 0.75 cm. In another embodiment of the methods of the present invention, the flanged proximal portion of the proximally-flaring stent is approximately 1.0 cm. In another embodiment of the methods of the present invention, the flanged proximal portion of the proximally-flaring stent is between approximately 0.25 cm and approximately 1.0 cm.

In one embodiment of the methods of the present invention, the proximally-flaring stent is made from an elastic metal or polymer. In another embodiment of the methods of the present invention, the proximally-flaring stent is made from a material selected from the group consisting of stainless steel, titanium, nickel-titanium, cobalt-chromium, cobalt-chromium-vanadium, cobalt-chromium-tungsten, gold, silver, platinum and platinum iridium or any combination thereof. In another embodiment of the methods of the present invention, the proximally-flaring stent is made from a material selected from the group consisting of biosorbable polymers, biodegradable polymers, bioerodable polymers and biologically stable polymers.

In one embodiment of the methods of the present invention, the proximally-flaring stent of the system further comprises a bioactive agent. In another embodiment of the methods of the present invention, the proximally-flaring stent further comprises a controlled release coating. In another embodiment of the methods of the present invention, the bioactive agent is selected from the group consisting of antiproliferatives, anti-thrombogenics, anti-coagulates, lubricity enhancing agents, anti-inflammatories, antibiotics, antioxidants and analgesics.

In one embodiment of the methods of the present invention, the balloons are segmented into one or more independently inflatable compartments. In another embodiment of the methods of the present invention, the distal portion of a balloon comprises a first compartment, the medial region comprises a second compartment and the proximal portion comprises a third compartment. In another embodiment of the methods of the present invention, during treatment of a treatment site with a vessel bifurcation, the compartment of each balloon that is closest to the vessel bifurcation is more compliant than the compartments that are farther from the vessel bifurcation. In another embodiment of the methods of the present invention, sequentially-inflatable balloons are made so by crimping different portions of the balloon onto the balloon catheter with different pressures.

The present invention also includes methods of deploying the system of the present invention. In one embodiment of the methods of the present invention, the system is deployed within a side branch of a branched vessel, such that the distal portion and medial region of the proximally-flaring stent expand within the side branch, the hinge area expands at the ostium and the flanged proximal portion of the proximally-flaring stent expands within the main artery giving rise to the side branch.

In one embodiment of the methods of the present invention, the method includes treating or inhibiting restenosis at a treatment site at a vascular bifurcation having a branch and a main artery, wherein the branch and main artery each have an inner luminal wall, by: advancing a two balloon system of the present invention to the treatment site at the vascular bifurcation; maneuvering the stent and first balloon into a branch of the vascular bifurcation, such that the distal portion and medial region of the proximally-flaring stent enter the branch, the hinge area is aligned approximately with the ostium and wherein the flanged proximal portion of the proximally-flaring stent is within the main artery; positioning the second balloon in the main artery; inflating the first balloon so that the distal portion and medial region of the proximally-flaring stent expand and contact the inner luminal wall of the branch, the hinge area expands and contacts the ostium and a portion of the flanged proximal portion expands and contacts the inner luminal wall of the main artery; deflating the first balloon; removing the first balloon from the treatment site; inflating the second balloon in the main artery sequentially from its proximal portion, to its medial region to its distal portion so that the portion of the flanged proximal portion of the stent not expanded by inflation of the first balloon is expanded to contact the inner luminal wall of the main artery; deflating the second balloon; and withdrawing the balloons and balloon catheter from the treatment site.

In one embodiment of the methods of the present invention, the method includes treating or inhibiting restenosis at a treatment site at a vascular bifurcation having a branch and a main artery, wherein the branch and the main artery each have an inner luminal wall, by: advancing a one balloon system of the present invention to the treatment site at the vascular bifurcation; maneuvering the system into the branch of the vascular bifurcation, such that the distal portion and the medial region of the proximally-flaring stent enter the branch, the hinge area is aligned approximately with the ostium and wherein the flanged proximal portion of the proximally-flaring stent is within the main artery; inflating the balloon; deflating the balloon and withdrawing the balloon and balloon catheter from the treatment site. In an alternative embodiment, the balloon can inflate sequentially from its distal portion, medial region and proximal portion respectively, so that the distal portion and the medial region of the proximally-flaring stent expand in a similar sequential manner and contact the inner luminal wall of the branch, the hinge area expands and contacts the ostium and wherein the flanged proximal portion expands last and contacts the inner luminal wall of the main artery of the vascular bifurcation.

In alternative embodiments of the present invention, the systems and methods can include flanged proximal portions of the proximally-flaring that further comprise self-expanding spring actions.

BRIEF DESCRIPTION OF THE DRAWINGS

In the accompanying drawings:

FIG. 3A depicts a partial cross-sectional view, illustrating the placement of one embodiment of the proximally-flaring stent and balloon catheter system of the present invention within a side branch of a branched vessel.

FIG. 3B depicts a partial cross-sectional view, illustrating deployment of the stent in the side branch of the branched vessel after inflation of a first balloon has occurred and the first balloon has been deflated and removed from the treatment site.

FIG. 3C depicts a partial cross-sectional view, illustrating inflation of a second balloon in the main artery (before it has been deflated) that completes deployment of the flanged proximal portion of the proximally-flaring stent within the main artery.

DETAILED DESCRIPTION OF PREFERRED EMBODIMENTS

Figure 1:
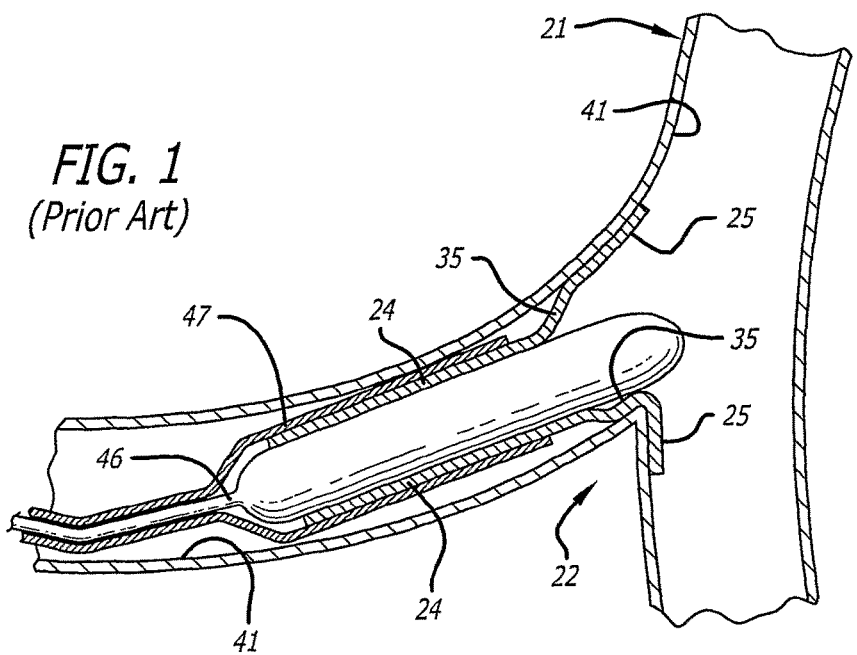
FIG. 1 depicts a perspective view of one embodiment of the distally-flaring stent described in the Lam patent.

The phrases "main vessel" and "main artery" mean any vessel or duct within the body that has one or more branches extending off of it. The use of the term "main" may suggest that the "main artery" is more substantial or bigger than its branch or branches, however, this relationship is not required. A "main vessel" or "main artery" can be larger than, smaller than, or equal in size to its branches.

The term "branch" and the phrase "side branch" mean any vessel or duct within the body that finds its origination point at another vessel or duct within the body. A branch can be larger than, smaller than, or equal in size to its originating lumen.

The term "body" refers to the physical substance of a human or animal, living or dead.

Previously-used stents did not provide a means to treat a lesion found primarily at an ostium and within the side branch of an artery when the branch could only be approached from the direction of the main artery (such as in the coronary arteries). For instance, the distally-flaring stents described in the Lam patent were inadequate to treat such lesions because if the distally-flaring portion of the stent was positioned in the immediate area of an ostium, the main portion of the distally-flaring stent was left within the main artery, and the lesion within the side branch was left untreated. If the distally-flaring end of the distally-flaring stent was positioned entirely within the side branch in an effort to restore patency there, the flaring portion of the stent had moved beyond the ostium that it was designed to treat and was no longer able to expand into the irregular shape of this area of the vessel. Instead, once positioned within a side branch, the distally-flaring portion of the distally-flaring stent was confined within the more uniform lumen of the vessel, removed a distance from the ostium. Thus, although the side branch of the artery may have been treated, the ostium was not.

The present invention solves the problems encountered by distally-flaring stents by providing proximally-flaring stent and balloon catheter systems ("the systems") and methods of using the same. In use, the systems are positioned within the side branch of a branched vessel. Unlike the distally-flaring stent described in the Lam patent, the flanged proximal portion of the proximally-flaring stent does not pass the ostium when positioned within a side branch. Thus, this proximally-flaring stent is able to treat a lesion found in a side branch that can only be approached from the direction of the main artery while still able to treat the irregular shape of its ostium.

A first embodiment of the system and methods of the present invention includes two balloon catheters each including an inflatable balloon. In this embodiment, the proximally-flaring stent is mounted onto the balloon of the first balloon catheter and positioned within a side branch. The second balloon catheter and its inflatable balloon are positioned within the main artery. During deployment of this embodiment of the systems of the present invention, the first balloon within the side branch is inflated, deflated and then withdrawn from the treatment site. This inflation of the first balloon deploys the portion of the proximally-flaring stent of the present invention within the side branch, and at the ostium and a portion of the flanged proximal portion of the stent within the main artery. In one embodiment, inflation of the first balloon deploys approximately ¼ to approximately ⅓ of the flanges of the flanged proximal portion of the proximally flaring stent. This inflation of the first balloon, however, does not fully deploy the flanged proximal portion of the proximally-flaring stent at the ostium and within the main artery. Instead, sequential inflation of the second balloon positioned within the main artery, from this balloon's proximal portion to its distal portion, completes the deployment of the flanged proximal portion of the proximally-flaring stent within the main artery.

In another deployment method of the systems of the present invention, the proximally-flaring stent is deployed with one balloon catheter. In this deployment method, the proximally-flaring stent is mounted onto an inflatable balloon that is then positioned within a side branch. In this deployment method, the proximal portion of the inflatable balloon extends proximally beyond the flanged proximal portion of the proximally-flaring stent. Due to the positioning of the proximal portion of the inflatable balloon relative to the flanged proximal portion of the proximally-flaring stent, inflation of the balloon can push the flanged proximal portion of the proximally-flaring stent entirely against the artery walls of the main artery so that blood flow is not occluded.

Figure 2:
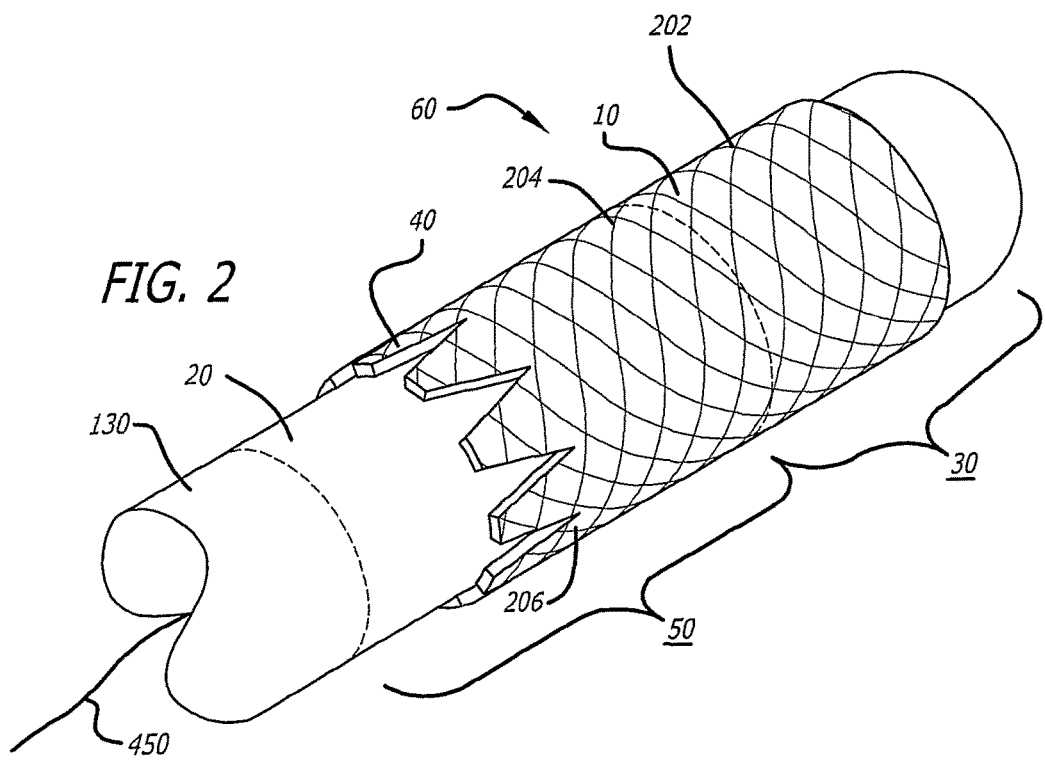
FIG. 2 depicts a proximally-flaring stent and balloon system of the present invention.
Figure 4A:
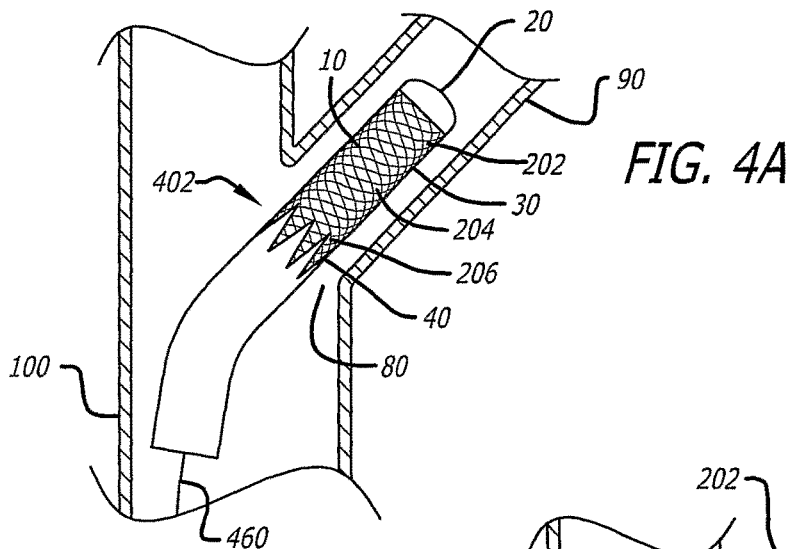
FIG. 4A depicts a partial cross-sectional view, illustrating the placement of an alternative embodiment of the proximally-flaring stent and balloon catheter system of the present invention within a side branch of a branched vessel.
Figure 4B:
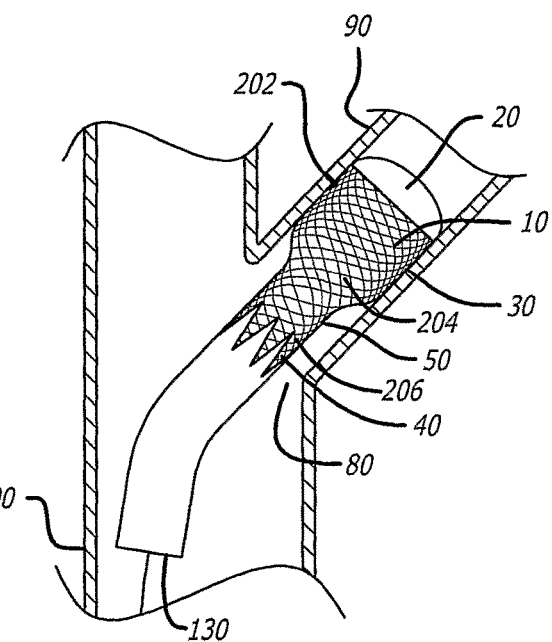
FIG. 4B depicts a partial cross-sectional view, illustrating the beginning of inflation of the balloon and subsequent expansion of the proximally-flaring stent of the present invention during deployment of the proximally-flaring stent.
Figure 4C:
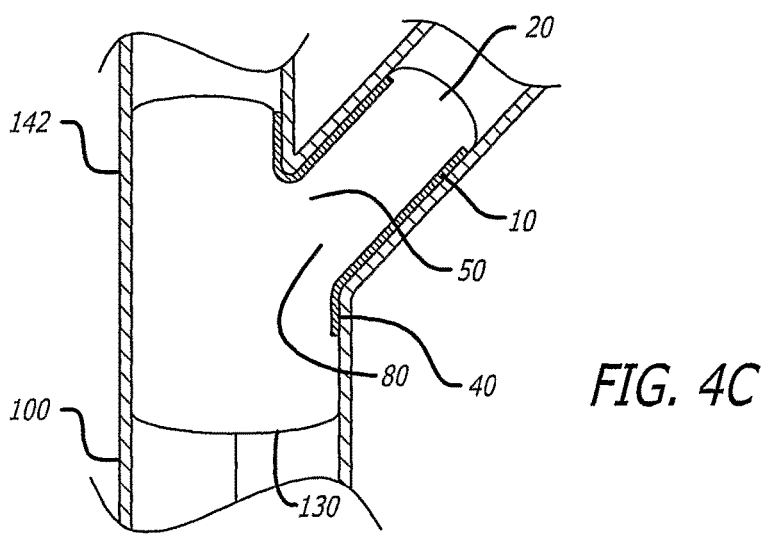
FIG. 4C depicts a partial cross-sectional view, illustrating the proximally-flaring stent of the present invention in expanded form after inflation of the balloon is complete in one deployment method of the present invention.

Referring to the Figures, FIG. 1 depicts a distally-flaring stent as described in the Lam patent. FIG. 2 depicts one embodiment of the proximally-flaring stent and balloon catheter systems of the present invention. FIGS. 3A through 3C depict a deployment method of the proximally-flaring stent of the present invention using a two balloon catheter system of the present invention. FIGS. 4A through 4C depict a deployment method of the proximally-flaring stent using a one balloon catheter system of the present invention. These systems and methods are depicted and described herein in order to better explain the invention. It will be understood that the systems and methods shown are representative only, and that systems of other configurations, sizes and styles as well as variations of the methods are within the scope of this invention.

FIG. 2 depicts one embodiment of the proximally-flaring stent and balloon catheter system 60 of the present invention. As contrasted to the distally-flaring stent of the Lam patent (FIG. 1), the system 60 comprises a proximally-flaring stent 10, a balloon catheter 450, and an inflatable balloon 20. The proximally-flaring stent 10 has a distal portion 202, a medial region 204, and a hinge area 206, and a flanged proximal portion 40. The hinge area 206 is the point on the proximally-flaring stent 10 where the medial region 204 and the flanged proximal portion 40 meet. The balloon catheter 450 has an inflatable balloon 20 with a distal portion 30, a medial region 50 and a proximal portion 130. In some embodiments of the present invention (i.e. when the balloon does not sequentially inflate), the portions of the inflatable balloon are only designated for positioning of the flanged proximal portion of the proximally-flaring stent and do not designate any differing characteristics or capabilities. In other embodiments of the present invention (for example and without limitation, when the balloon is sequentially inflatable), the portions of the balloon can adopt different characteristics or capabilities. When the proximally-flaring stent 10 is mounted onto the balloon 20, the flanged proximal portion 40 of the proximally-flaring stent 10 constitutes the flaring portion and, in one embodiment, is found within the medial region 50 of the balloon 20. In another embodiment, the proximally-flaring stent 10 covers approximately the distal half of the balloon 20. In both of these embodiments, at least a portion of the medial region 50 of the balloon 20 and the proximal portion 130 of the balloon 20 will inflate substantially proximally beyond the flanged proximal portion 40, thus ensuring that the flanged proximal portion 40 of the proximally-flaring stent 10 is pressed flush against the inner lumen of the main artery so that blood flow within the main artery is not occluded. The distal portion 202 of the proximally-flaring stent 10 is distal to the flanged proximal portion 40. This depicted embodiment can be used with the two or the one balloon catheter systems and deployment methods.

FIGS. 3A-3C depict one embodiment and deployment method of the present invention using two balloon catheters. In this embodiment (FIG. 3A), the proximally-flaring stent 10 again includes a distal portion 202, a medial region 204, a hinge area 206, and a flanged proximal portion 40. The first balloon catheter 250 includes a first inflatable balloon 260 with a proximal portion 110, a medial region 111 and a distal portion 112. In this embodiment, the areas of the first balloon are only designated for purposes of placement of the flanged proximal portion of the proximally-flaring stent. A second balloon catheter 400 includes a second inflatable balloon 270 that also includes a proximal portion 280, a medial region 290 and a distal portion 300. In this embodiment of the system of the present invention, the proximally-flaring stent 10 is mounted on the first balloon 260.

In this embodiment of the stent 10 and balloon catheter (250 & 400) system 401, the proximally-flaring stent 10 is deployed by inflation of both balloons 260 and 270. First, the balloon 260 and proximally-flaring stent 10 are positioned within a side branch 90 and the second balloon 270 is positioned within the main artery. The first balloon is then inflated to deploy the majority of the proximally-flaring stent 10. In one embodiment this balloon inflation deposits the distal portion 202, and the medial region 204 of the proximally flaring stent 10 within the side branch 90, the hinge area 206 at the ostium and approximately ¼ to approximately ⅓ of the flanges of the flanged proximal portion 40 against the walls of the main artery. The first balloon 260 then is deflated and removed from the treatment site. In this embodiment, inflation of the first balloon 260 does not entirely deploy the flanged proximal portion 40 (i.e., the remaining ⅔ to ¾ of the flanges) of the proximally flaring stent 10. FIG. 3B depicts a non-deployed portion 320 of the flanged proximal portion 40 of the proximally-flaring stent 10 after the first balloon 260 has been inflated, deflated and removed from the treatment site. As shown in FIG. 3C, full deployment of the flanged proximal portion 40 of the proximally-flaring stent 10 then is achieved by inflating the second balloon 270 positioned within the main artery from its proximal portion 280 through its medial region 290 and finally through its distal portion 300. Note that in this embodiment the first balloon 260 could be modified to achieve sequential inflation, but it does not need to be so modified. Indeed, the balloons positioned within the side branch in any embodiment of the present invention can consist of a single balloon that is uniformly inflatable. Finally, while not required, inflation of the second balloon 270 can also deploy a stent within the main artery (i.e. the second balloon can be delivered "alone" or with a stent mounted onto it).

FIGS. 4A through 4C depict a deployment method for a one balloon proximally-flaring stent 10 and balloon catheter 460 system 402 of the present invention. FIG. 4A depicts placement of the proximally-flaring stent 10 and balloon catheter 460 system 402 within a side branch 90 of a branched vessel 100. Note that, while not required, the balloon carrying the proximally-flaring stent depicted in this FIG. 4 does include sequential inflation capabilities. In this embodiment, the distal portion 30 of the balloon 20 is positioned within the side branch 90 of a branched vessel 100 so that the distal portion 202, and medial region 204 of the proximally-flaring stent 10 are within the side branch 90, the hinge area 206 is approximately flush with the ostium 80 and the flanged proximal portion 40 of the proximally-flaring stent 10 is within the main artery 100.

FIG. 4B depicts the sequential inflation of the balloon 20 in this deployment method of the present invention. In this figure, the distal portion 30 of the balloon 20 has inflated while the medial region 50 and proximal portion 130 of the balloon 20 have not yet fully inflated. At this stage of proximally-flaring stent 10 deployment, the inflation of the distal portion 30 of the balloon 20 expands and deploys the distal portion 202 of the proximally-flaring stent 10. The medial region 204, the hinge area 206 and the flanged proximal portion 40 of the proximally-flaring stent 10 are not yet fully deployed.

In FIG. 4C inflation of the balloon 20 is complete. Inflation has progressed through the medial region 50 of the balloon 20 through the proximal portion 130 of the balloon 20. The balloon 20 inflates to conform to the irregular shape of the branched vessel 100 so that the hinge area 206 and the flanged proximal portion 40 of the proximally-flaring stent 10 covers the ostium 80 of the branched vessel 100 and a small portion of the walls of the main artery 142 respectively.

As will be understood by one of skill in the art, for the proximal portion 130 of the balloon 20 to expand to conform to the irregular shape of an ostium 80 in this embodiment of the present invention, this portion of the balloon 20 must be sufficiently compliant. Such compliance along the entire length of the balloon 20 could negatively affect the proximally-flaring stent's 10 deliverability. Thus, in one embodiment of the balloon 20 of the present invention, the balloon's 20 distal portion 30 and medial region 50 are less compliant than the proximal portion 130 so that deliverability of the proximally-flaring stent 10 is maintained.

Certain, but not all embodiments of the balloons of the present invention require sequential inflation. This sequential inflation can be accomplished by means known to those of skill in the art. For instance, the rigidity or tensile strength of the material with which the balloons are manufactured can be adjusted such that the application of pressure from within the balloon expands the "weaker" portions first. Alternatively, the sequential inflation of the balloons also can be accomplished through the use of independently-inflatable compartments. Depending on the deployment method chosen, these inflation compartments also can have the same or different rigidities or tensile strengths to maintain the deliverability of the proximally-flaring stent yet provide a compliant enough portion of the balloon that can expand into the irregular shape of an ostium. Further, sequential inflation can be achieved by varying the amount of pressure used to crimp various portions of the inflatable balloon onto the balloon catheter. Specifically, a portion of an inflatable balloon crimped onto a balloon catheter with less pressure will inflate before a portion of the balloon crimped onto the balloon catheter with more pressure. Thus, as will be understood by one of skill in the art, depending on the inflation characteristics desired in a given balloon, appropriate pressures and crimping locations can be chosen.

The cross section of the proximally-flaring stent of the present invention can expand radially upon deployment within a vessel or duct lumen. The proximally-flaring stent of the present invention will have adequate radial strength to maintain its expanded cross-sectional area once the force causing its expansion is removed. Adequate radial strength can be accomplished through the use of an appropriate material as well as by the use of an appropriate geometric structural configuration.

In accordance with the ability to radially-expand and maintain its expanded shape, the proximally-flaring stent of the present invention can be manufactured using appropriate materials and methods known to those of skill in the art. For instance, the starting material of the proximally-flaring stent can be a thin tube of a metal or alloy such as, without limitation, stainless steel, titanium, tantalum, nitinol, Elgiloy® (a registered trademark of Combined Metals of Chicago, LLC), NP35N and mixtures thereof. Materials that may be memory-retaining for shape also can be used in accordance with the present invention. For instance, memory-retaining materials appropriate for use with the present invention include, for example and without limitation, an appropriate alloy of nickel and titanium, or stainless steel. The proximally-flaring stent can be made at any length that is appropriate for use within the body and with any appropriate slot or wire configuration. The proximally-flaring stent can be cut into the appropriate slot or wire configuration using laser etching, computer programmable, high precision laser etching, electrical discharge machining (EDM), chemical or photochemical etching as well as through the use of a precision jig. Regarding the material of the proximally-flaring stent of the present invention, the material can have a low metal-to-space ratio.

As will be apparent to one of skill in the art, the configurations and lengths of the proximally-flaring stent 10 itself as well as the configuration and length of the flanged proximal portion 40 can be adjusted to meet particular treatment objectives. The components of the system of the present invention also can take various forms in relation to one another. For example, in one embodiment of the present invention, the flanged proximal portion can be made of the same material as that of the non-flaring portion. In another particular embodiment, the proximally-flaring and non-flaring portions of the proximally-flaring stent can be constructed of different materials. Further, in one embodiment of the present invention, the flanged proximal portion of the proximally-flaring stent can be continuous with the non-flaring portion of the proximally-flaring stent. In another embodiment, the proximally-flaring and non-flaring portions of the proximally-flaring stent can be two or more separate and distinct parts that have been attached. To improve positioning during use, radiopaque markers can be placed so as to mark the area of the proximally-flaring stent where the flaring and non-flaring portions meet.

The flanged proximal portion of the proximally-flaring stent of the present invention can be highly malleable and capable of expanding into a variety of irregular shapes. In order to achieve these characteristics, the flanged proximal portion of the proximally flaring stent can include a plurality of individual petals. Each individual petal can be individually capable of adopting an undeformed configuration that is substantially parallel to the longitudinal axis of the proximally-flaring stent and a deformed configuration that is not parallel to the longitudinal axis of the proximally-flaring stent. Further, the flanged proximal portion of the proximally-flaring stent of the present invention can be capable of deforming throughout its length to varying degrees so that it can conform to the irregular shape of an ostium and its surrounding area. In one embodiment of the proximally-flaring stent of the present invention, the individual petals can be connected by a thin malleable material that enhances the conforming capability of the flanged proximal portion. In another particular embodiment, the flanged proximal portion can be manufactured from a material that accomplishes the flaring function, yet has no recognizable petals. In another embodiment of the proximally-flaring stent of the present invention, radiopaque markers can be placed to mark locations within the flanged proximal portion of the proximally-flaring stent to assist in positioning during clinical use. The flanged proximal portion of the proximally-flaring stent of the present invention can be between about 0.25 cm and about 1.0 cm. In one embodiment of the present invention, the flanged proximal portion can be about 0.25 cm. In another embodiment of the present invention, the flanged proximal portion can be about 0.50 cm. In another embodiment of the present invention, the flanged proximal portion can be about 0.75 cm. In yet another embodiment of the present invention, the flanged proximal portion can be about 1.0 cm.

The proximally-flaring stent of the present invention can be coated with an appropriate material to enhance its clinical performance. For instance, various coatings can be capable of releasing a drug or bioactive agent to assist in the repair of a diseased vessel and to assist in the prevention of restenosis. Further, as mentioned, the proximally-flaring stent of the present invention can be coated with a radioactive material, such as a radio-opaque dye or marker to allow for better positioning in radiopacity. These coating can be continuous or discontinuous on the surface of the proximally-flaring stent and can be disposed on the interior and/or the exterior surface(s) of the proximally-flaring stent. Coatings can include one or more layers and can be coated either directly onto the proximally-flaring stent or onto a primer material on the proximally-flaring stent.

Any coating placed on the proximally-flaring stent of the present invention should be biocompatible in order to minimize adverse interaction with the walls of the vessel or duct lumen or with the liquid flowing through the lumen. The coating can consist of a polymeric coating material. In one embodiment of the present invention the polymeric coating can have zwitterionic pendant groups, generally ammonium phosphate ester groups, for instance phosphoryl choline groups, or analogues thereof. Other examples of suitable polymers can be found in published International patent applications WO-A-93/16479 and WO-A-93/15775 which are hereby incorporated by reference. Coatings used in accordance with the present invention also can consist of nonpolymeric coating materials.

Many substances that can enhance clinical performance can be included in coatings of the proximally-flaring stent of the present invention. For instance, a radioactive material, such as a radio-opaque dye or marker can be used to allow for better positioning during radiopacity. These markers can be placed on the ends of the proximally-flaring stents as well as to mark the location of the beginning and/or ends of the flanged proximal portion. Drugs and bioactive agents that can enhance the clinical performance of the proximally-flaring stent of the present invention also can be included. Examples of such drugs and bioactive agents include, for example and without limitation, antineoplastic, antiinflammatory, antiplatelet, anticoagulant, antifibrin, antithrombin, antimitotic, antibiotic, antiproliferative and antioxidant substances, as well as calcium channel blockers, colchicine fibroblast growth factor antagonists, histamine antagonists, HMG-CoA reductase inhibitors, monoclonal antibodies, phosphodiesterase inhibitors, prostaglandin inhibitors, platelet-derived growth factor antagonists, serotonin inhibitors, steroids, and thioprotease inhibitors. Additional substances can include, for example and without limitation, rapamycin, cladribine, heparin, nitrous oxide, nitric oxide, actinomycin D, as well as, alpha-interferon, genetically engineered epithelial cells, and fish oil (omega 3-fatty acid).

In one embodiment of the present invention, the cross-sectional area of the proximally-flaring stent is increased by exerting force upon the internal walls of the proximally-flaring stent. For instance, one or more inflatable balloons can exert force on the internal walls of the proximally-flaring stent. The proximally-flaring stent of the present invention also could be self-expanding. For instance, the proximally-flaring stent of the present invention can be embodied in a shape memory material, including, for example and without limitation, an appropriate alloy of nickel and titanium, or stainless steel. In this embodiment after the proximally-flaring stent has been formed, it can be compressed so that it is small enough to permit insertion into a vessel or duct. Such insertion can occur through the use of a appropriate catheter or flexible rod known to those of skill in the art. On emerging from the catheter or flexible rod, the proximally-flaring stent can expand into the desired configuration automatically or such expansion can be triggered by a change in pressure, temperature or electrical stimulation. In another embodiment, the proximally-flaring stent of the present invention can be comprised of a spring-like material and loaded onto a retaining sleeve. Upon removal of the retaining sleeve, the proximally-flaring stent expands and the flaring portion opens, thereby securing the proximally-flaring stent within the diseased portion of the bifurcated vessel. In yet another embodiment of the proximally-flaring stent of the present invention, only a portion of the proximally-flaring stent can comprise spring-like material. In this configuration, deformation or expansion of the portion of the proximally-flaring stent that is not comprised of spring-like material can be accomplished by other means, such as, without limitation, balloon expansion.

The inflatable balloons of the present invention can be formed with many different materials including, for example and without limitation, polyethylene, polyolefin copolymer, polyethylene teraphthalate, nylon, and PeBax® (a registered trademark of Alkema, Inc.)

The proximally-flaring stent of the present invention can be used in any blood vessel, including, for example and without limitation, the coronary vasculature (which includes the right, left common, left anterior descending and circumflex arteries and their branches) and the peripheral vasculature (including branches of the carotid, aorta, femoral, renal, popliteal, and related arteries). While the proximally-flaring stent of the present invention mainly has been described in terms of its use in a blood vessel, it can also be used in other lumens of the body, for example and without limitation, respiratory ducts, gastrointestinal ducts, bile ducts, the urinary system, the digestive tube, and the tubes of the reproductive system in both men and women.

It is to be understood that the present invention is not limited to the particular embodiments, materials, and examples described herein, as these can vary. It also is to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "a stent" or "a balloon catheter" is a reference to one or more stents or balloon catheters and includes equivalents thereof known to those skilled in the art and so forth.

Unless defined otherwise, all technical terms used herein have the same meanings as commonly understood by one of ordinary skill in the art to which this invention belongs. Specific methods, devices, and materials are described, although any methods and materials similar or equivalent to those described herein can be used in the practice or testing of the present invention.

I claim:

1. A system for deploying a stent, the system comprising:
    a proximally-flaring stent having:
        (a) a first distal portion;
        (b) a first medial region;
        (c) a hinge area; and
        (d) a flanged proximal portion including flanges;
    a first balloon catheter having a first inflatable balloon with:
        (a) a second distal portion;
        (b) a second medial region; and
        (c) a proximal portion; and
    a second, separate balloon catheter having a second inflatable balloon with
        (a) a third distal portion;
        (b) a third medial region; and
        (c) a third proximal portion;
    wherein:
        (a) the first inflatable balloon is not capable of sequential inflation and inflation of the first inflatable balloon is configured to deploy approximately ¼ to approximately ⅓ of the flanges of the flanged proximal portion of the proximally flaring stent, and wherein the first inflatable balloon is configured to solely position the flanges of the flanged proximal portion at an ostium within a main artery; and
        (b) the second inflation balloon is configured to inflate sequentially from the third proximal portion to the third distal portion to deploy the flanges of the proximally flaring stent not deployed by the first inflatable balloon, and wherein the second inflatable balloon does not include a stent.

2. The system of claim 1, wherein the system is deployed within a side branch of a branched vessel, such that:
    (a) the first distal portion and the first medial region expand within the side branch;
    (b) the hinge area expands at the ostium; and
    (c) the flanged proximal portion expands within a main artery or conduit giving rise to the side branch.

3. The system of claim 1, wherein the proximally-flaring stent is made from an elastic metal or polymer.

4. The system of claim 3, wherein the elastic metal is selected from the group consisting of stainless steel, titanium, nickel-titanium, cobalt-chromium, cobalt-chromium-vanadium, cobalt-chromium-tungsten, gold, silver, platinum and platinum iridium or any combination thereof.

5. The system of claim 3, wherein the polymer is selected from the group consisting of biosorbable polymers, biodegradable polymers, bioerodable polymers and biologically stable polymers.

6. The system of claim 3, further comprising a bioactive agent.

7. The system of claim 6, wherein the bioactive agent further comprises a controlled release coating.

8. The system of claim 6, wherein the bioactive agent is selected from the group consisting of anti proliferatives, anti-thrombogenics, anti-coagulates, lubricity enhancing agents, anti-inflammatories, antibiotics, antioxidants and analgesics.

9. The system of claim 1, wherein the second inflatable balloon is sequentially-inflatable due to segmentation into one or more independently inflatable compartments.

10. The system of claim 1, wherein the second inflatable balloon is differentially crimped.

11. The system of claim 1, wherein the proximally-flaring stent is deployed in the direction of blood flow in a vessel.

12. A method comprising:
    providing a proximally-flaring stent comprising a first distal portion, a first medial region, a hinge area and a flanged proximal portion including flanges;
    providing a first balloon catheter having a first inflatable balloon having a second distal portion, a second medial region, and a proximal portion, wherein the first inflatable balloon is not capable of sequential inflation and wherein the first inflatable balloon is configured to solely position the flanges of the flanged proximal portion at an ostium within a main artery; and
    providing a second, separate balloon catheter having a second inflatable balloon wherein the second inflatable balloon does not include a stent and comprises a third distal region, a third medial region, and a third proximal portion;
    wherein the proximally-flaring stent is mounted onto the first inflatable balloon such that the flanged proximal portion of the proximally-flaring stent:
        (a) does not extend proximally beyond the first inflatable balloon's medial portion;
        (b) is proximal to the proximally-flaring stent's distal portion; and
        (c) the flanges of the proximally flaring stent not deployed by the first inflatable balloon are deployed by sequential inflation of the second inflatable balloon of the second, separate balloon catheter from the third proximal portion to the third distal portion.

13. The method of claim 12, wherein the proximally-flaring stent is made from an elastic metal or polymer.

14. The method of claim 13, wherein the elastic metal is selected from the group consisting of stainless steel, titanium, nickel-titanium, cobalt-chromium, cobalt-chromium-vanadium, cobalt-chromium-tungsten, gold, silver, platinum and platinum iridium or any combination thereof.

15. The method of claim 13, wherein the polymer is selected from the group consisting of biosorbable polymers, biodegradable polymers, bioerodable polymers and biologically stable polymers.

16. The method of claim 13, further comprising a bioactive agent.

17. The method of claim 16, wherein the bioactive agent further comprises a controlled release coating.

18. The method of claim 12, wherein the second inflatable balloon is made sequentially inflatable by crimping the balloon onto the second balloon catheter with varying pressures such that:
  (a) the third distal portion of the second inflatable balloon is crimped onto the second, separate balloon catheter with the most pressure;
  (b) the third proximal portion is crimped onto the second, separate balloon catheter with the least pressure; and
  (c) the third medial region is crimped onto the second, separate balloon catheter with an amount of pressure between that applied to the third distal portion and the third proximal portion.

19. The method of claim 12, wherein the second inflatable balloon is segmented into one or more independently inflatable compartments.

20. The method of claim 12, wherein the proximally-flaring stent is deployed in the direction of blood flow in a vessel.

* * * * *